United States Patent [19]
Ringpfeil

[11] Patent Number: 5,981,233
[45] Date of Patent: Nov. 9, 1999

[54] PROCESS FOR MANUFACTURING A XYLANASE ENZYME COMPLEX FROM PRE-TREATED THIN STILLAGE OF RYE

[75] Inventor: Manfred Ringpfeil, Berlin, Germany

[73] Assignee: Roche Vitamins Inc., Parsipanny, N.J.

[21] Appl. No.: 09/130,331

[22] Filed: Aug. 6, 1998

[30] Foreign Application Priority Data

Aug. 21, 1997 [EP] European Pat. Off. .............. 97114431

[51] Int. Cl.⁶ .............................. C12P 21/04; C12N 9/24; C12N 1/14
[52] U.S. Cl. ...................... 435/71.1; 435/200; 435/254.6
[58] Field of Search .................................. 435/71.1, 200, 435/254.1, 254.6

[56] References Cited

FOREIGN PATENT DOCUMENTS

| 2041859 | 5/1991 | Canada . |
|---|---|---|
| 455 928 | 12/1990 | European Pat. Off. . |
| 278 359 | 5/1990 | Germany . |
| 40 17 522 | 5/1990 | Germany . |
| 291 673 | 7/1991 | Germany . |

OTHER PUBLICATIONS

Viesturs et al. "Production of cellulases and xylanases by *Trichoderma viride* and biological processing of lignocellulose and recycled paper fibers," Appl. Biochem. Biotechnol. (1996) vol. 57/58, p. 349–360.

Yinbo et al. "Production, charaterization, and application of the cellulase–free xylanase from *Aspergillus niger*," Appl. Biochem. Biotechnol. (1996) vol. 57/58, p. 375–381.

"Biotechnology", Rehm, Ed. (1987) (VCH: Fed Rep. Germany) p. 75–85 and 136–144, 1987.

J. Broz, Mh. Vet.–Med., 48:213–217 (1993).

M. Bailey et al., Appl. Microbiol. Biotechnol., 40:224–229 (1993).

R. Haapala et al., Enzyme and Microbial Technology, 18:495–501 (1996).

J. Szczodark, Acta Biotechnol., 8:509–515 (1988).

M. Bailey et al., World of Journal of Microbiology and Biotechnology, 9:80–84 (1993).

M. Karni et al., World of Journal of Microbiology and Biotechnology, 9:476–478 (1993).

M. Hoq et al., Appl. Microbiol. Biotechnol., 43:604–609 (1995).

R. Haapala et al., Appl. Microbiol. Biotechnol., 43:815–821 (1995).

H. Purkarthofer et al., Enzyme and Microbial. Technology, 17:114–118 (1995).

B. Montenecourt, Trends in Biotechnology, 1(5):156–160 (1983).

Derwent Abstract Accession No. 91–362461/50 (Patent No. DE 4017522).

Derwent Abstract Accession No. 90–305647/41 (Patent No. DD 278359).

Derwent Abstract Accession No. 88–257384/37 (Patent No. DD 291673).

*Primary Examiner*—Jon P. Weber
*Assistant Examiner*—Susan Hanley
*Attorney, Agent, or Firm*—Mark E. Waddell; Stephen M. Haracz; Brave Cave LLP

[57] ABSTRACT

A process is disclosed for manufacturing a xylanase-rich enzyme complex by cultivating a xylanase-producing microorganism of the genus Trichoderma in a nutrient medium involves cultivating said microorganism in a nutrient medium containing a pre-treated thin stillage of rye as both the xylanase inductor and the carbon source. Pre-treatment of the thin stillage comprises removing the solid constituents of the thin stillage of rye, concentrating the non-volatile components by evaporation of water and other volatile substances, and autoclaving the thin stillage of rye concentrate resulting therefrom. De-oiled soya meal or soya meal liquor can be used as an additional xylanase inductor and as a nitrogen source. Addition of the de-oiled soya meal or soya meal liquor to the pre-treated thin stillage of rye further increases the xylanase production. The enzyme complexes so manufactured can be used immediately in the animal feedstuff industry such as poultry feeds. The use of said enzyme complexes in rye-, barley- or triticale-containing feedstuffs reduces the antinutritive action of the non-starch polysaccharides, leading to improved digestability and absorption of the nutrients in an animal's intestine.

18 Claims, No Drawings

PROCESS FOR MANUFACTURING A XYLANASE ENZYME COMPLEX FROM PRE-TREATED THIN STILLAGE OF RYE

BACKGROUND OF THE INVENTION

1. Field

The present invention is a fermentative process for manufacturing xylanase-rich enzyme complexes. Pre-treated thin stillage of rye acts as an inductor for xylanase formation.

2. Description

Xylanase is a hemicellulase enzyme which hydrolyzes xylans (also called "wood gums") to xylose and other sugars. The enzyme is also known as endo-1,4-β-D-xylanase or 1,4-β-D-xylan xylanohydrolase and belongs to the EC 3.2.1.8 enzyme class. Xylans are polysaccarides formed from 1,4-β-glycoside-linked D-xylopyranoses with short side-chains of different composition, and can contain arabinose, glucose, galactose and/or glucuronic acid as well as acetyl and methyl groups in the molecule. Xylans are components of many deciduous and coniferous trees, as well as cereals, bran, pectin, tragacanth, plant gums, etc. Xylans are structurally diverse. Therefore, complete degradation of branched, partially acetylated xylans requires the action of a variety of xylanases to hydrolyze the xylans to xylose and other sugars. The mode of action of xylanases is complex and is realized in conjunction with other (to some extent synergistic) enzymes.

Xylanases are formed by fungi (for example, Trichoderma, Penicillium, Aspergillus, Talaromyces and Sporotrichum) and bacteria (for example, Clostridium, Cellulomonas, Bacillus, Thermononspora and Ruminococcus). Xylanases are used in the cellulose industry as bleaching and improving agents, and have been recently utilized in the manufacture of animal feed. Studies indicate that exogenous enzymes, such as xylanases, added to animal feeds containing rye, barley or triticale (1) favorably reduce the antinutritive action of the non-starch polysaccharides and (2) improve digestibility and absorption of the nutrients in the intestine of the animal. The most important enzymes (used extensively in broiler rearing) can hydrolyze the non-starch polysaccharides present in cereal types such as, barley, wheat, and rye. Several preparations containing such enzymes are already on the market. For example, Roxazyme® G (Roche) contains cellulase, β-glucanase, and xylanase. Such preparations are admixed with the animal feed to achieve the mentioned advantages. Xylanase-rich enzyme complexes manufactured in accordance with the subject invention are useful for producing these preparations. The use of xylanase as a feed additive in poultry nutrition is an important application. Substantially increased nutritive value of broiler feed can be achieved with energy-poor cereal types, such as barley, oats, rye, and triticale [see Mh. Vet.-Med. 48: 213–217 (1993) and the references cited therein].

Attempts have been made to selectively increase the xylanolytic activity of xylanase producing microorganisms. Xylan-containing substances have been added to nutrient medium (fermentation medium) to induce xylanase formation. Purified xylans, wheat bran, barley glume, milled maize cobs (maize spindle flour), straw, and thin stillage of rye are examples of these substances. By such means it is possible to increase xylanase activity [see as technological background German Patent Specifications DD 278 359 and DD 291 673; European Patent Publication (EP) 0 455 928 A1; Appl. Microbiol. Biotechnol., 40: 224–229 (1993); and Enzyme & Microb. Technol., 18: 495–501 (1996)]. This inductor effect can be achieved in a cost-effective manner using thin stillage of rye. Unfortunately, however, increasing concentrations of thin stillage of rye inhibits the growth and enzyme formation of the described microorganisms.

The present invention provides a process for manufacturing xylanase-rich enzyme complexes using cost effective thin stillage of rye.

SUMMARY OF THE INVENTION

The subject invention provides a process for manufacturing a xylanase-rich enzyme complex by cultivating a xylanase-producing microorganism of the genus Trichoderma in a nutrient medium. This process comprises: a) producing an inductor from thin stillage of rye and b) culturing a xylanase-producing microorganism of the genus Trichoderma in the presence of the inductor and a nutrient medium. The inductor is produced by: 1) removing solid constituents from the thin stillage of rye, to produce a resultant; 2) concentrating the resultant by evaporating water and other volatile substances from the resultant to form a concentrate; and 3) autoclaving the concentrate.

DETAILED DESCRIPTION OF THE INVENTION

The subject invention will now be described in terms of its preferred embodiments. These embodiments are set forth to aid in understanding the invention but are not to be construed as limiting.

The present invention is a process for manufacturing enzyme complexes by cultivating a xylanase-producing microorganism of the genus Trichoderma in a nutrient medium containing carbon sources, nitrogen sources, and particular salts. The xylanase-rich (and at the same time cellulase- and β-glucanase-reduced) enzyme complex formed in the nutrient medium is then isolated. Microorganisms of the genus Trichoderma are effective as formers of enzymes having polysaccharolytic activity with clear preference for cellulolytic activity (i.e. the activity is preferably directed towards the degradation of cellulose).

Surprising, it has been found that a special pre-treatment of the thin stillage of rye to be used as the inductor counteracts the disadvantageous inhibiting activity of the native thin stillage of rye while at the same time increasing inductor activity. This pre-treated thin stillage of rye acts as both the agent for the induction of the xylanase formation (hereinafter denoted as "xylanase inductor") and the carbon source. The pre-treatment comprises removing a substantial portion, preferably substantively all, of the solid constituents of the thin stillage of rye. Non-volatile components are concentrated by evaporation of water and other volatile substances. Subsequently, the thin stillage of rye resulting therefrom is autoclaved. The enzyme formation induced as a consequence of the treatment and realized during the cultivation of the microorganism (in the fermenter) gives rise to a significant change in the enzyme spectrum: first, the xylanolytic activity exceeds by several hundred percent the activity of the other enzymes (i.e. the cellulolytic and glucanolytic activity); and second, the xylanase to cellulase ratio is shifted in favor of xylanase.

Xylanase-producing microorganisms of the genus Trichoderma useful in the present invention include, Trichoderma (T.) reesei mutants derived from the wild strain QM6a, for example, QM 9123, QM 9414, M 18.2, M 18.2-y, Rut M-7 and Rut NG-14 (see Bland S. Montenecourt, "Trichoderma reesei cellulases", Trends in Biotechnology, Vol. 1, No. 5, pages 156–160, 1983 and the references cited therein).

Some of the above-mentioned microorganism strains have been deposited, namely

QM6a: ATCC 13631, CCM F-560, CMI 45548, DSM 768;
QM 9123: ATCC 24449;
QM 9414: ATCC 26921, CCM F-522, DSM 769;
M 18.2: DSM 10683;
M18.2-y: DSM 7537.

Microorganism strains *T. reesei* QM 6a, QM 9123 and QM 9414 are listed in Catalogues of International Depositary Authorities, e.g. the Deutsche Sammlung von Mikroorganismen und Zellkulturen GmbH ("DSM") and/or the American Type Culture Collection ("ATCC"), and as such are commercially available from these and other sources. The microorganism strain M 18.2 was deposited at the DSM on May 14, 1996 by Biopract GmbH, Rudower Chaussee 5, D-12489 Berlin, for long-term storage, and was allotted the deposit no. DSM 10683; on Jun. 12, 1998 the DSM received a request from Biopract GmbH to convert the deposit into one under the Budapest Treaty. Finally, the microorganism strain M 18.2-y was originally deposited on Aug. 31, 1989 at the Zentralinstitut für mikrobielle und experimentelle Therapie ("ZIMET") in Jena under the Budapest Treaty and allotted the deposit no. IMET 43915. On Mar. 4, 1993 this strain was transferred to the DSM in Braunschweig and given the new deposit no. DSM 7537. Through ownership changes the microorganism strain *T. reesei* M 18.2-y eventually became the property of F. Hoffmann-La Roche AG.

The pre-treated thin stillage of rye used in the subject process functions both as the xylanase inductor and the carbon source, and originates from thin stillage (vinasse or distillery "slops") obtained from grain distilleries. Normally, such thin stillage is considered a waste product. The (untreated) thin stillage of rye results when spirits are produced from rye. Such spirits are produced by fermenting rye, water and enzymes (exo- and endo-glucanases). In this fermentation, rye starch is converted to alcohol by yeast over a period of about three days at about 30° C. After distillation of the alcohol, the mixture (largely free from rye starch) remains as the thin stillage of rye.

The composition of the thin stillage of rye differs between batches as is typical of natural products. This stillage of rye comprises predominantly carbohydrates (cellulose, hemicellulose, pentosans), small amounts of albumins, mineral substances and fats as well as residual amounts of ethanol and other byproducts of yeast fermentation.

In the subject invention, pre-treatment of the thin stillage of rye comprises (1) removing solids, (2) concentrating non-volatile components, and (3) autoclaving the concentrate obtained. These pre-treatment steps typically have the following preferred features:

Removing the solid constituents of the thin stillage of rye by decantation and separation using a plate separator (e.g. of the type SA 1 Westfalia Separator AG, Oelde, Germany). The volume of the solid-containing fraction to be discarded amounts to about 30% to about 50% of the volume of the thin stillage of rye.

Concentrating the non-volatile components of the solid-free thin stillage of rye using a vacuum rotary evaporator (for example, of the type VUV 20-I, Schott & Gen, Jena, Germany) at a boiling temperature lying between about 40° C. and about 50° C. and at the vapor pressure of the solid-free thin stillage of rye corresponding to the temperature. Under these conditions the volume of the solid-free thin stillage of rye is reduced by about 80% to about 90% after about 1 hour.

The concentration of the non-volatile components accordingly amounts to about 1:5 to about 1:10 (about a five- to about ten-fold increase in concentration).

Autoclaving the concentrated, solid-free thin stillage of rye for at least about 30 minutes at about 121° C. (conveniently 121±1° C.).

In addition to the pre-treated thin stillage of rye, other carbon sources can be used in the nutrient medium, for example, lactose, cellulose, xylans, wheat bran, glucose syrup and spray-dried corn steep liquor. Especially preferred additional carbon sources include lactose, cellulose and oat glume xylan.

Acceptable nitrogen sources for the nutrient medium include ammonium sulphate [$(NH_4)_2SO_4$], ammonia-water [$NH_3-H_2O$] and de-oiled soya meal (as an organic nitrogen source). The nitrogen content conveniently amounts to at least 20% based on the carbon source.

Potassium dihydrogen phosphate ($KH_2PO_4$) can be used as the phosphorus source for the nutrient medium. The phosphorus content conveniently amounts to at least 2.5% based on the carbon source.

The nutrient medium can contain additional salts, such as magnesium sulphate, iron sulphate, manganese sulphate, zinc sulphate, calcium chloride, and cobalt chloride.

The nutrient medium can also contain an antifoam agent, such as M-30 (Serva Feinbiochemica, Heidelberg, Germany), Glanapon DG 102 (Bussetti, Vienna, Austria) or MAZU 8005 (Quest International, Cork, Ireland).

The present invention conveniently uses about 35 to about 45 g/l, preferably about 40 g/l, of a ten-fold concentrated pre-treated thin stillage of rye based on the total volume of the culture medium. The volume of the inoculum for *Trichoderma reesei* typically amounts to about 10% of the total volume of the culture medium.

The pH value for the cultivation conveniently lies in the range of about 5.5 to about 6.5, preferably at about 6.0. The adjustment of the pH value in the culture medium is conveniently effected with ammonia-water in a concentration of about 12.5% to about 25% (based on $NH_3$).

The cultivation temperature is conveniently about 28° C. to about 34° C., preferably about 31° C.

The fermentation apparatus used can be a conventional cultivation vessel (fermenter) for which precautions have been taken to exclude foreign infections. Such cultivation vessels normally include a stirring arrangement and a gasification arrangement for the air supply (an aerobic submersed culture of the microorganism). The stirring speed and air supply are conveniently regulated such that the oxygen content in the culture medium does not fall below about 10% of the oxygen saturation value.

Especially suitable for carrying out the subject process is the so-called "fed batch technique", in which the first step (batch phase) comprises a batch fermentation, followed by a substrate introduction step (fed batch phase).

The batch phase serves for the cultivation of mycelium in the nutrient medium, whereby the injection (inoculation) of the fermenter is conveniently effected in three stages (i)–(iii):

(i) rinsing of the conidia of a slanted agar culture from the stock reserve of microorganisms with sterilized tap water. The water conveniently contains an emulsifier, e.g. Tween® 80 (preferably in this case in a concentration of about 1 g/l). The conidia suspension is suitably adjusted to at least $5 \times 10^8$ conidia/l, especially $5 \times 10^8 - 1 \times 10^9$/l.

(ii) Shaking flasks suitably containing known nutrient media for microorganisms of the genus *Trichoderma reesei* on the basis of glucose or cellulose as C-source, phosphate, nitrate, urea, peptone and trace elements [see for example R. Haapala, E. Parkkinen, P. Suominen and S. Linko, "Production of extracellular enzymes by immobilized *Trichoderma reesei* in shake flask cultures", Appl. Microbiol. Biotechnol. 43, 815–821 (1995)] are injected with the conidia suspension produced in stage (i). The ratio by volume of conidia suspension to nutrient medium is conveniently about 1:25 to about 1:50. In these shaking flasks the conidia are cultivated at about 31° C.±1° C. (30–32° C.), conveniently at about 31° C., and with a shaking frequency of about 200 to about 300 rpm, preferably about 250 rpm, up to the point at which a culture medium with well-branched mycelium has become formed. No formation of spores should be recognizable.

(iii) The fermenter is injected with the culture medium produced in stage (ii), such that the ratio by volume of the culture medium to the nutrient medium in the fermenter is conveniently about 1:5 to about 1:10, preferably about 1:5.

The enzyme formation takes place mainly in the subsequent fed batch phase. The addition of the substrate solution (substrate introduction), preferably of pre-treated thin stillage of rye, as the inductor, of de-oiled soya meal or soya meal liquor as the organic nitrogen source as well as of lactose as the carbon source is suitably regulated by means of a control device or an analytically-supported process control of the specific carbon dioxide evolution of the mycelium. The substrate introduction can be controlled, for example, by means of the carbon dioxide concentration of the exhaust gas from the fermentation or can be performed according to an empirically determined time regime.

In a further aspect of the present invention, additional de-oiled soya meal or soya meal liquor is used as an (additional) nitrogen source. A further increase in xylanase production can be achieved by adding de-oiled soya meal or of soya meal liquor to the pre-treated thin stillage of rye. It is assumed that the de-oiled soya meal or the soya meal liquor has the action of a xylanase inductor.

De-oiled soya meal is typically a commercial product of soya milling. Concentration of the de-oiled soya meal in the culture medium is conveniently between about 20 and about 30 g/l nutrient medium in the batch phase and conveniently between about 15 and about 25 g/l substrate solution in the fed batch phase, preferably about 25 g/l and about 20 g/l, respectively.

The soya meal liquor which is alternatively used is an aqueous solution of ingredients of the de-oiled soya meal. Soya meal liquor is produced by suspending de-oiled soya meal in water (about 35 g/l). The suspension is boiled for about 10 minutes and, after cooling to room temperature, the solid constituents are filtered off. The volume of the solid-free filtrate (soya meal liquor) amounts to about 80% of the volume of the soya meal suspension prior to the filtration. Soya meal liquor is used as an alternative to the de-oiled soya meal preferably in the fed batch phase, with the volume of the soya meal liquor corresponding to the weighed amount of de-oiled soya meal.

The separation of the enzyme complex produced in accordance with the invention and its purification and concentration can be performed according to methods known per se. Basic requirements for this are low media temperatures (about 5° C. to about 15° C.) and low pH values (about 4 to about 4.5) as well as aseptic conditions. The procedure conveniently involves:

Separating the biomass from the fermentation medium by centrifugation or filtration as well as microfiltration;

concentrating the enzyme complex by ultrafiltration;

for the production of a solid enzyme preparation, spray drying the concentrated enzyme complex.

The main field of application for the subject enzyme complex is its utilization as a feed additive in animal feed. The enzyme complex can be used as the non-worked up fermentation medium, as the culture filtrate, as the enzyme concentrate, or as a solid preparation.

The present invention is illustrated by the following Example.

EXAMPLE

A xylanase-rich enzyme complex was manufactured using *Trichoderma reesei* M 18.2-y (DSM 7537) in a fed batch fermentation.

For the production of the thin stillage of rye concentrate, the solid-free fraction of a thin stillage of rye was concentrated 7.5-fold under vacuum at about 50° C. and autoclaved at 121° C. for about 30 minutes.

For the production of the nutrient medium for the batch phase, 1800 ml of nutrient medium consisting of 20.8 g/l lactose, 8.3 g/l microcrystalline cellulose, 25 g/l de-oiled soya meal, 33.3 ml/l thin stillage of rye concentrate, 3.75 g/l $KH_2PO_4$, 6.0 g/l $(NH_4)_2SO_4$, 0.5 g/l $MgSO_4.7H_2O$, 0.5 g/l $CaCl_2.2H_2O$, 6.25 mg/l $FeSO_4.7H_2O$, 2.0 mg/l $MnSO_4.H_2O$, 1.75 mg/l $ZnSO_4.7H_2O$ and 2.5 mg/l $CoCl_2.6H_2O$ were autoclaved at 121° C. in a 5 l fermenter for 20 minutes and adjusted to pH 6.0 with 12.5% ammonia-water.

For the production of the substrate solution for the fed batch phase, 1000 ml of the substrate and inductor solution consisting of 300 g/l lactose, 10 g/l cellulose, 500 ml/l of soya meal liquor and 107 ml/l thin stillage of rye concentrate were autoclaved at 121° C. for 20 minutes. (For the production of the 500 ml of soya meal liquor, 20 g of soya meal were suspended in 600 ml of water; the suspension was boiled for 10 minutes and the solid content was filtered off.)

In the batch phase the fermenter was inoculated with 300 ml of shaking flask pre-culture. To prepare the appropriate inoculate about 3 ml each of sterilized tap water containing 1 g/l TWEEN®80 (polyethoxysorbitane oleate) were introduced into two slanted agar tubes from the stock reserve, and the conidia from both agar surfaces were shaken off. In the following stage three shaking flasks each containing 100 ml of nutrient medium were injected with equal volumes the conidia suspension. The nutrient medium consisted of 20 g/l of glucose, 15.0 g/l of $KH_2PO_4$, 4.8 g/l of $(NH_4)_2SO_4$, 0.3 g/l of $CaCl_2.2H_2O$, 0.3 g/l of $MgSO_4.7H_2O$, 5.0 mg/l of $FeSO_4.7H_2O$, 1.6 mg/l of $MnSO_4.H_2O$, 1,4 mg/l of $ZnSO_4.7H_2O$ and 2.0 mg/l of $CoCl_2.6H_2O$. Then the shaking flask precultures were cultivated at 31° C. and a shaking frequency of about 250 rpm. The pH value of the medium was not adjusted or regulated. At the start of the cultivation the pH value was about 5, at the end about 3.5. After a cultivation period of about 28 hours the fermenter was injected with these shaking flask precultures. Then the pH value was adjusted to 6.0 with 12% ammonia-water. The oxygen content was held at about 10% of the oxygen saturation value at 31° C. using stirrer cascade regulation. After cultivation for 21 hours a first $CO_2$ maximum in the fermenter exhaust gas was exceeded, and thus the end of the batch phase had been reached.

For the fed batch phase the discontinuous addition of the substrate was commenced after the $CO_2$ content in the exhaust gas had fallen to 80% of the first maximum. Each addition led to a further $CO_2$ maximum. The additions were effected portionwise automatically after the $CO_2$ content in the exhaust gas had fallen to 80% of the previous maximum. The added volumes of the substrate solution corresponded to an addition of 1.5 g of lactose per liter of culture medium and of 2.0 g of lactose per liter of culture medium from 50 hours fermentation.

The fermentation was ended after 72 hours by cooling to 10° C. and adjusting the pH value to 4.5. The mycelium was filtered off and the residual fermentation solution was subjected to analysis. The enzyme activities in the fermentation medium were:

| | |
|---|---|
| Xylanase: | 2625 U/ml |
| β-Glucanase: | 555 U/ml |
| Carboxymethylcellulase (CMCase): | 330 U/ml |

The concentration of dissolved proteins in the fermentation medium amounted to 17.0 g/l.

Enzyme and Protein Determinations

The activity of the xylanase (endo-1,4-β-xylanase) was determined by incubation with a 0.5% xylan suspension (xylan from oat glume, Roth) in 40 mM sodium acetate buffer (pH 6.0) at 50° C. for 20 minutes. One unit (U) of xylanase released 1 mol of xylose per minute.

The activity of the β-glucanase (endo-1,3-1,4-β-glucanase) was determined by incubation with a 0.5% lichenin suspension (lichenin, Carl Roth GmbH, Karlsruhe, Germany) in 40 mM sodium acetate buffer (pH 6.0) at 50° C. for 20 minutes.

The activity of the CMCase (endo-1,4-β-glucanase) was determined by incubation with a 2.0% solution of carboxymethylcellulose sodium salt (Carl Roth GmbH) in 40 mM sodium acetate buffer (pH 6.0) at 50° C. for 20 minutes. One unit (U) of β-glucanase or CMCase released 1 mol of glucose per minute.

The protein determination was carried out following a protein precipitation (addition of trichloroacetic acid) using a modified method according to Lowry based on bicinchonic acid: Sigma Procedure No. TPRO-562 (Sigma Chemical Co., St. Louis, USA).

What is claimed is:

1. A process for manufacturing an enzyme complex comprising xylanase by cultivating a xylanase-producing microorganism of the genus Trichoderma in a nutrient medium, which process comprises:
   a) producing an inductor from thin stillage of rye by
      1) removing solid constituents from the thin stillage of rye, to produce a resultant,
      2) concentrating said resultant by evaporating water and other volatile substances from said resultant to form a concentrate, and
      3) autoclaving said concentrate to form said inductor;
   b) culturing the xylanase-producing microorganism of the genus Trichoderma in a nutrient medium, wherein said nutrient medium comprises said inductor; and
   c) recovering the enzyme complex.

2. The process according to claim 1, wherein removing solid constituents comprises decanting and separating using a plate separator.

3. The process according to claim 1, wherein concentrating the resultant comprises rotary vacuum evaporation.

4. The process according to claim 3, wherein the rotary vacuum evaporation is performed between about 40° C. and about 50° C. and at reduced pressure so that the volume of the resultant is reduced by about 80% to about 90% after about one hour.

5. The process according to claim 1, wherein autoclaving the concentrate is carried out for at least about 30 minutes at about 121° C.

6. The process according to claim 1, wherein the microorganism of the genus Trichoderma is a *Trichoderma reesei*.

7. The process according to claim 6, wherein the *Trichoderma reesei* microorganism is obtained from the wild strain QM6A.

8. The process according to claim 7, wherein the *Trichoderma reesei* is selected from the group consisting of QM 9123, QM 9414, M 18.2, M 18.2-y, Rut M-7, and Rut NG-14.

9. The process according to claim 1, wherein said nutrient medium comprises one or more substances selected from the group consisting of lactose, cellulose, xylans, wheat bran, glucose syrup, and spray-dried corn steep liquor.

10. The process according to claim 9, wherein said nutrient medium comprises lactose, cellulose and oat glume xylan.

11. The process according to claim 1, wherein said nutrient medium comprises one or more substances selected from the group consisting of ammonium sulphate, ammonia water, and de-oiled soya meal.

12. The process according to claim 1, wherein said nutrient medium comprises a phosphorus source.

13. The process according to claim 12, wherein the phosphorus source is potassium dihydrogen phosphate.

14. The process according to claim 1, wherein said nutrient medium comprises one or more salts selected from the group consisting of magnesium sulphate, iron sulphate, manganese sulphate, zinc sulphate, calcium chloride, and cobalt chloride.

15. The process according to claim 1, wherein the culturing is at a pH between about 5.5 and about 6.5, and at a temperature between about 28° C. and about 34° C.

16. The process according to claim 1, wherein said nutrient medium comprises de-oiled soya meal or soya meal liquor.

17. The process according to claim 1, wherein the culturing is performed using a fed batch technique.

18. The process according to claim 4, wherein the reduced pressure is the vapor pressure at the boiling temperature of said resultant.

* * * * *